(12) United States Patent
Krivoruchko

(10) Patent No.: US 8,747,353 B2
(45) Date of Patent: Jun. 10, 2014

(54) CATHETER BALLOON HAVING IMPROVED FLEXIBILITY AND METHODS FOR MAKING SAME

(75) Inventor: Michael Krivoruchko, Forestville, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 2119 days.

(21) Appl. No.: 11/733,402

(22) Filed: Apr. 10, 2007

(65) Prior Publication Data

US 2008/0255511 A1 Oct. 16, 2008

(51) Int. Cl.
*A61M 31/00* (2006.01)

(52) U.S. Cl.
USPC ...................... 604/103.08; 604/509

(58) Field of Classification Search
USPC ............ 604/96.01, 103.01, 103.2, 103.8, 509
See application file for complete search history.

(56) References Cited

U.S. PATENT DOCUMENTS

| | | | |
|---|---|---|---|
| 3,953,566 A | 4/1976 | Gore | |
| 4,187,390 A | 2/1980 | Gore | |
| 5,078,727 A | 1/1992 | Hannam et al. | |
| 5,458,568 A | 10/1995 | Racchini et al. | |
| 5,709,653 A | 1/1998 | Leone | |
| 6,120,477 A | 9/2000 | Campbell et al. | |
| 6,585,926 B1* | 7/2003 | Mirzaee | 264/400 |
| 6,663,590 B2 | 12/2003 | Blatter | |
| 6,923,827 B2 | 8/2005 | Campbell et al. | |
| 2004/0122464 A1* | 6/2004 | Wang et al. | 606/194 |
| 2006/0136032 A1 | 6/2006 | Legarda et al. | |

FOREIGN PATENT DOCUMENTS

| | | |
|---|---|---|
| EP | 1388346 | 4/2006 |
| GB | 1566674 | 2/1978 |
| WO | WO97/02791 | 1/1997 |
| WO | WO97/10871 | 3/1997 |

OTHER PUBLICATIONS

Written Opinion of the International Searching Authority for PCT/US2008/058291.

* cited by examiner

*Primary Examiner* — Quynh-Nhu H Vu
*Assistant Examiner* — Brandy S Lee

(57) ABSTRACT

A method for manufacturing a balloon catheter assembly includes forming a balloon from a polymer selected from the group consisting of polyamide, polyether block amide, and polyethylene terephthalate, forming a plurality of pores in the polymer, and mounting the balloon onto a catheter shaft. The shaft is configured to supply a fluid to the balloon to inflate the balloon, and the pores are configured to prevent the fluid from passing through the balloon.

16 Claims, 3 Drawing Sheets

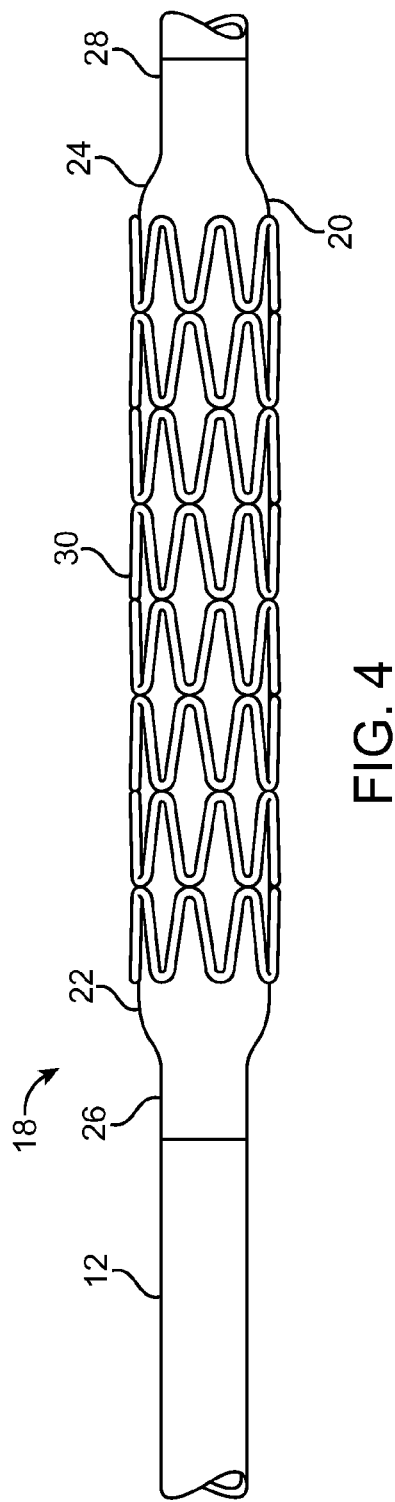
FIG. 4
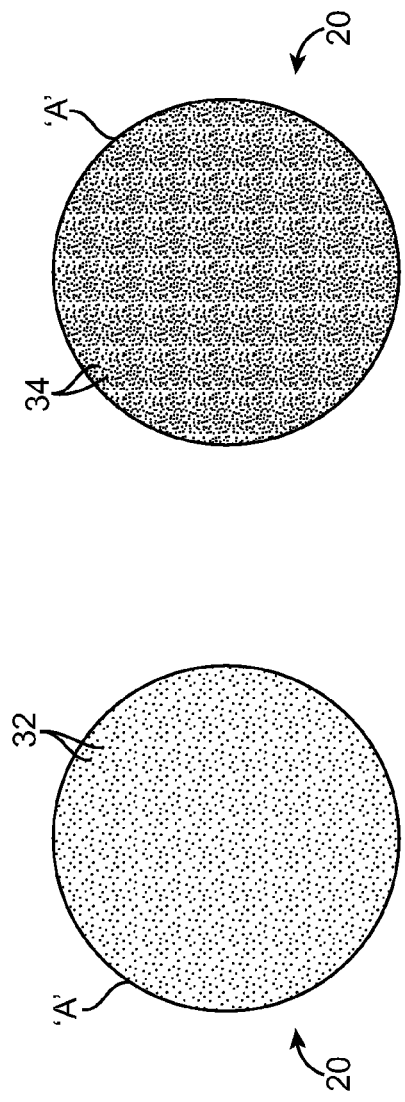
FIG. 5
FIG. 6

CATHETER BALLOON HAVING IMPROVED FLEXIBILITY AND METHODS FOR MAKING SAME

BACKGROUND OF THE INVENTION

1. Field of the Invention

The present invention generally relates to balloon catheters, and more specifically relates to balloons for balloon catheters that have improved flexibility and methods for making such balloons.

2. Description of Related Art

Percutaneous transluminal angioplasty (PTCA) is used to open coronary arteries, which have been occluded by a build-up of cholesterol fats or atherosclerotic plaque. Typically, a guide catheter is inserted into a major artery in the groin and is passed to the heart, providing a conduit to the ostia of the coronary arteries from outside the body. A balloon catheter and guidewire are advanced through the guiding catheter and steered through the coronary vasculature to the site of therapy. The balloon at the distal end of the catheter is inflated, causing the site of the stenosis to widen. Dilation of the occlusion, however, can form flaps, fissures or dissections, which may threaten, re-closure of the dilated vessel. Implantation of a stent can provide support for such flaps and dissections and thereby prevent reclosure of the vessel. Reducing the possibility of restenosis after angioplasty may reduce the likelihood that a secondary angioplasty procedure or a surgical bypass operation will be needed.

A stent is typically a hollow, generally cylindrical device formed from wire(s) or a tube, and is deployed in a body lumen from a radially contracted configuration into a radially expanded configuration, which allows it to contact and support the vessel wall. A plastically deformable stent can be implanted during an angioplasty procedure by using a balloon catheter bearing the compressed or "crimped" stent, which has been loaded onto the balloon. The stent radially expands as the balloon is inflated, forcing the stent into contact with the body lumen, thereby forming a support for the vessel wall. Deployment is effected after the stent has been introduced percutaneously, transported transluminally and positioned at a desired location by means of the balloon catheter.

A balloon of appropriate size and pressure may be first used to open the lesion. The process can be repeated with a stent loaded onto a balloon. A direct stenting procedure involves simultaneously performing angioplasty and stent implantation using a stent mounted on a dilatation balloon. After the balloon is withdrawn, the stent remains as a scaffold for the injured vessel.

The overall performance of the balloon may depend on the flexibility and strength of the balloon. If the balloon does not exhibit enough flexibility, the delivery of the balloon and the stent may be impeded, as it may be more difficult to navigate through the torturous path of the vessels if the balloon is too stiff. However, soft balloons with higher flexibility may not have enough hoop strength to effectively open a lesion and/or expand a stent.

It is desirable to provide a stent balloon assembly with a balloon having improved flexibility and enough hoop strength to open a lesion and/or expand the stent.

SUMMARY OF THE INVENTION

It is an aspect of the present invention to provide a method for manufacturing a more flexible balloon catheter assembly.

In an embodiment, a method for manufacturing a balloon catheter assembly is provided. The method includes forming a balloon from a polymer selected from the group consisting of polyamide, polyether block amide, polyethylene, and polyethylene terephthalate, forming a plurality of pores in the polymer, and mounting the balloon onto a catheter shaft. The shaft is configured to supply a fluid to the balloon to inflate the balloon, and the pores are configured to prevent the fluid from passing through the balloon.

It is another aspect of the present invention to provide a more flexible balloon catheter assembly.

In an embodiment, a balloon catheter assembly is provided. The balloon catheter assembly includes a catheter shaft, and a balloon mounted on the catheter shaft. The catheter shaft is configured to deliver an inflation fluid to the balloon. The balloon includes a polymer selected from the group consisting of polyamide, polyether block amide, polyethylene, and polyethylene terephthalate, and a plurality of pores in the polymer. The pores is constructed and arranged to block fluid from passing therethrough when the balloon is inflated by the fluid.

The foregoing and other features and advantages of the invention will become further apparent from the following detailed description of the presently preferred embodiments, read in conjunction with the accompanying drawings. The detailed description and drawings are merely illustrative of the invention, rather than limiting the scope of the invention being defined by the appended claims and equivalents thereof.

BRIEF DESCRIPTION OF THE DRAWINGS

Embodiments of the present invention will now be described, by way of example only, with reference to the accompanying schematic drawings in which corresponding reference symbols indicate corresponding parts, and in which:

FIG. 4 is a detailed view of detail 'A' in FIG. 2 according to an embodiment of the present invention; and FIGS. 5 and 6 are detailed views of detail 'A' in FIG. 2 according to alternative embodiments of the present invention having different numbers of pores per surface area of the balloon.

DETAILED DESCRIPTION OF EMBODIMENTS OF THE INVENTION

Figure 1:
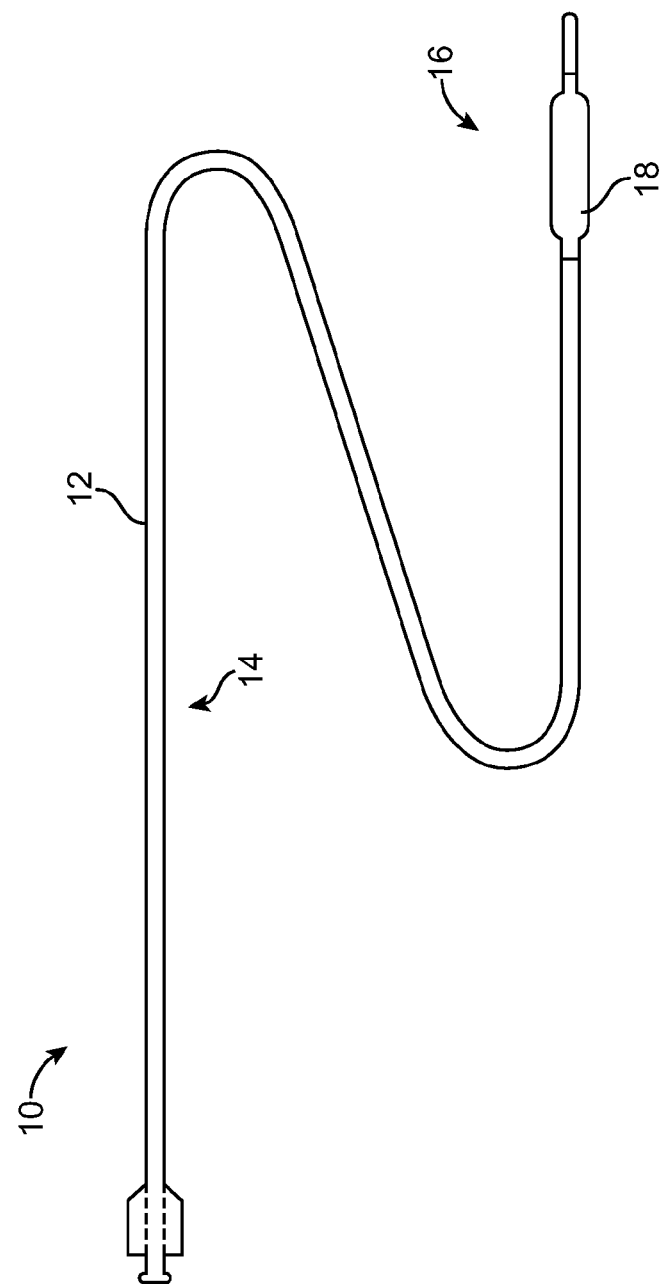
FIG. 1 is a schematic side view of a balloon catheter assembly according to embodiments of the present invention.

FIG. 1 illustrates a balloon catheter assembly 10 according to embodiments of the present invention. As illustrated, the assembly 10 includes a catheter shaft 12 having a proximal section 14 and a distal section 16, and a balloon 18 mounted to the distal section 16 of the shaft 12.

The shaft 12 may be made from any suitable material known in the art, including but not limited to polyamides, polyolefins, and polyesters, and may be formed by any suitable process, such as extrusion or injection molding, known in the art.

According to embodiments of the present invention, the balloon 18 may be used in a wide range of applications, including but not limited to cardiovascular, neurovascular and peripheral applications. For example, the balloon may be used as a dilatation balloon for an angioplasty procedure, or a stent delivery balloon for delivering stents to a targeted site, as well as other applications.

While the balloons of the present invention can vary in size, and can be used for different applications, they should exhibit the unique mechanical response described herein, namely, they exhibit low profile, high hoop strength, and high trackability, without allowing fluid to pass through the balloon.

Figure 2:
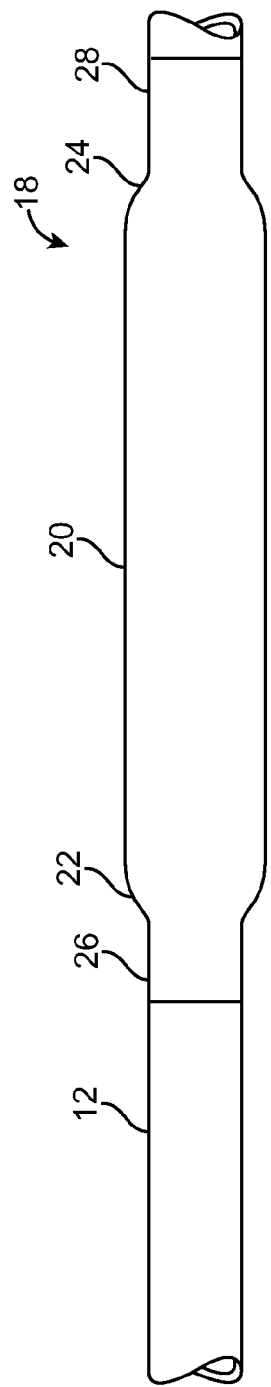
FIG. 2 is a schematic side view of the balloon catheter assembly of FIG. 1 after the balloon has been expanded.
Figure 3:
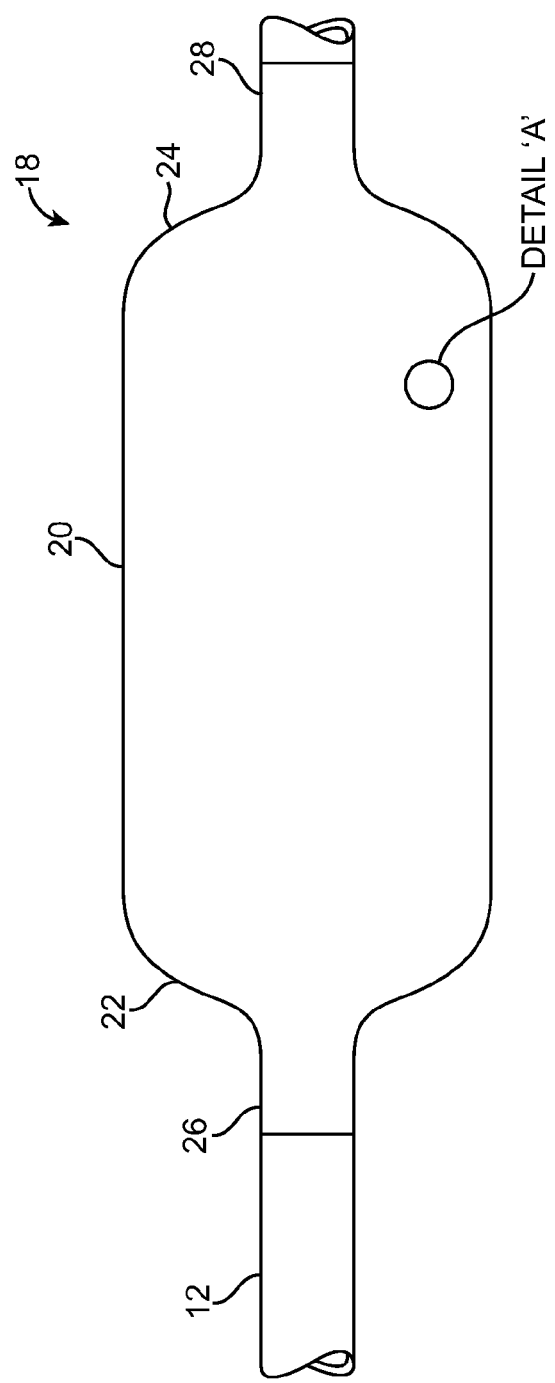
FIG. 3 is a schematic side view of a balloon catheter assembly according to another embodiment of the present invention.

As illustrated in FIGS. 2 and 3, the balloon 18 includes a body portion 20 that is substantially cylindrical in shape when the balloon 18 is inflated. A first tapered section 22 extends from one end of the body portion 20 and a second tapered section 24 extends from the other end of the body portion 20. A first neck portion 26 extends from the first tapered section 22 on an opposite side as the body portion 20, and a second neck portion 28 extends from the second tapered section 24 on an opposite side of the body portion 20. The first and second neck portions 26, 28 are configured to be connected to the catheter shaft 12. The balloon 18 may be attached to the shaft 12 by known methods, such as adhesive bonding, thermal bonding, and/or laser bonding.

FIG. 4 illustrates another embodiment of the balloon catheter assembly of the present invention. In this embodiment, a stent 30 is mounted to the body portion 20 of the balloon. The stent 30 is configured to be radially expanded by the balloon upon inflation of the balloon. Any suitable radially expandable stent may be used, so specific details of the stent 30 are not discussed herein.

The balloon 18 may be made from a suitable polymeric material that may be reduced in density without negatively impacting the physical properties of the balloon 18, as will be discussed in further detail below. The polymeric material is preferably selected from the group consisting of polyamide, such as nylon-12, polyether block amide, such as PEBAX®, polyethylene, and polyethylene terephthalate ("PET"), although it is contemplated that other polymeric materials may be used within the context of the present invention.

For example, other polymeric materials that may be used in accordance with the present invention include but are not limited to polybutylene terephthalate, polyester elastomers that use a polyester as a hard segment, polyolefins, such as polyethylene or polypropylene, polyolefin elastomers, vinyl based polymers, such as polyvinyl chloride, polyvinylidene chloride, or polyvinylidene fluoride, polyamide elastomers, polyimides, polystyrenes, styrene-ethylene/butylene-styrene resins, polyurethanes, polyurethane elastomers, acrylonitrile butadiene styrene resins, acrylic resins, polyarylates, polycarbonates, polyoxymethylenes, polyvinyl alcohol, and fluorocarbon resins, such as ethylenetetrafluoroethylene, perfluoroalkoxy copolymer, and polytetrafluoroethylene. Polymer derivatives of these materials may also be used.

Dilatation or distensibility is used herein to refer to the expandability of the balloon. Balloons of the present invention are sufficiently expandable to treat various sized arteries, and for stent delivery. Preferably, balloons of the present invention are configured to have radial growths in the range of about 2% to about 40% between nominal and rated pressures. More preferably, the radial growth of the balloon is in the range of about 5% to about 20%.

Balloons of the present invention have sufficient hoop strengths that allow the balloons to be used in a variety of applications, for example, to dilate occluded vessels without bursting, and to successfully expand stents during delivery. Hoop strength is directly related to the maximum amount of pressure the balloon can withstand, for a given material and a given balloon wall thickness, without failing. The balloons of the present invention may have hoop strengths upon dilatation of about 12,000 to about 75,000 p.s.i. Preferably, balloons of the present invention have hoop strengths greater than about 14,000 p.s.i.

The balloons may be formed in a variety of ways. In one embodiment, an extruder may be used to melt process the polymer into a tube or some other shape that may be used as a balloon preform. The extruder may be part of an injection molding machine that may include a mold that is configured to shape the polymer into a balloon preform as the polymer cools. The balloon may be blow molded or stretch blow molded into the desired shape from the balloon preform, as is known in the art.

As shown in FIGS. 5 and 6, at least the body portion 20 of the balloon 18 includes a plurality of pores 32, 34. The pores are created in the polymer of the body portion 20 of the balloon 18 so as to create a balloon with increased flexibility. The size of the pores 32, 34 and the number of pores per surface area of the balloon (i.e., density) may be optimized for the specific operating parameters of the balloon 18. For example, the pores may be optimized for the specific inflation fluid used, balloon material, and operating pressure, so that the resulting catheter has improved flexibility and can accommodate the inflation pressure needed for the targeted application (e.g., angioplasty or stent delivery), but does not allow the inflation fluid to leak out of the balloon during inflation. For example, the average diameter of the pores may be less than about 500 μm (microns), preferably between about 0.1 micron and about 400 microns, and more preferably between about 1 micron and about 100 microns, and the pore population density (or distribution) in the balloon may range from about 100 pores per $cm^2$ to about 1,000,000 pores per $cm^2$. These examples of pore sizes and densities are not intended to be limiting in any way. FIG. 5 illustrates an embodiment in which the number of pores 32 per surface area of the balloon (i.e., density) is less than the number of pores 34 per surface area of the balloon illustrated in FIG. 6. The embodiments illustrated in FIGS. 5 and 6 are not intended to be limiting in any way.

The pores may be created by any suitable process. For example, in an embodiment, a solvent may be introduced into the polymer during melt processing. The solvent may be in a liquid form. The solubility parameter of the solvent is preferably about equal to the solubility parameter of the polymer. The solubility parameter is a numerical value that indicates the relative solvency behavior of a specific solvent. Solubility parameters for many solvents are well known in the art. The solvent may be selected so that it is soluble in the polymer during melt processing, but can be extracted out of the polymer as the polymer exists the melt processing equipment so as to leave pores in the polymer as the polymer cools. In another embodiment, a soluble gas may be injected into the polymer during melt processing so as to create cavities in the polymer as the polymer exits the processing equipment. The specific type and amount of liquid or gas injected into the polymer during melt processing will depend on the type of polymer and processing conditions used to create the balloon, as well as desired size and density of the pores in the polymer.

In another embodiment, rather than creating the pores during melt processing, the pores may be created after the polymer is cooled into a solid balloon preform, either before or after the preform is blow molded into a balloon. For example, the pores may be created with a laser or any other suitable ablation tool. In one embodiment, the pores may be created with a micro-punching tool that is constructed and arranged to mechanically create the pores by punching through the balloon in a controlled manner.

In another embodiment, the pores may be created as the balloon preform is stretched into the shape of the balloon. For example, U.S. Pat. No. 4,187,390 discloses a method for creating porous structures out of tetrafluoroethylene polymers. Similar methods may be used to create porous structures out of polyamides, polyether block amides, polyethylene, and polyethylene terephthalate in accordance with embodiments of the present invention. Specifically, once the balloon preform has been created, the preform may be reheated to a suitable temperature and stretched at a suitable strain rate, for the specific polymer being used, to create a node and fibril microstructure of the type described by U.S. Pat. No. 4,187,390. As would be appreciated by one of ordinary skill in the art, the size and distribution of the nodes and fibrils, and resulting pores, will depend on the temperature and strain rate used to stretch the balloon preform.

In another embodiment, micro or nano sized particles may be dispersed into the polymer during melt processing. When the balloon preform is blow molded into the shape of the balloon, the particles will create nucleation sites for the pores. The size and amount of particles may be selected based on the desired pore size and density in the balloon.

In another embodiment, the balloon may be created from oriented microfibers that are woven and/or heat fused together in a configuration that will leave small gaps or pores in an otherwise tightly packed structure. The gaps or pores may be of the size and density described above.

By creating pores in the balloon in accordance with embodiments of the present invention, the balloon will have a reduced density (as compared to the density of the solid polymer used to make the balloon), thereby creating a more flexible balloon. The open space created by the pores may allow for movement of the polymer during bending and flexing, thereby increasing the flexibility of the balloon during delivery to the targeted site in the lumen. The pores are also sized and distributed with a suitable (population) density to prevent the inflation fluid from exiting the balloon upon inflation, and also to prevent blood from entering the balloon when the balloon is in the vessel.

It will be understood by those skilled in the art that various changes in form and details may be made therein without departing from the spirit and scope of the present invention as defined in the appended claims. Thus, the breadth and scope of the present invention should not be limited by any of the above-described exemplary embodiments, but should be defined only in accordance with the following claims and their equivalents.

What is claimed is:

1. A method for manufacturing a balloon catheter assembly, the method comprising:
    forming a balloon from a polymer selected from the group consisting of polyamide, polyether block amide, polyethylene, and polyethylene terephthalate;
    forming a plurality of pores in the polymer; and
    mounting the balloon onto a catheter shaft, the shaft being constructed and arranged to supply a fluid to the balloon to inflate the balloon, the pores being sized and distributed to prevent the fluid from passing through the balloon.

2. A method according to claim 1, wherein the pores have an average diameter of less than about 500 microns.

3. A method according to claim 2, wherein the pores have an average diameter of greater than about 0.1 micron and less than about 400 microns.

4. A method according to claim 3, wherein the pores have an average diameter of between about 1 micron and about 100 microns.

5. A method according to claim 1, wherein said forming said pores is completed before said forming said balloon.

6. A method according to claim 1, wherein said forming said pores is completed after said forming said balloon.

7. A method according to claim 6, wherein said forming said pores comprises ablating said pores in said balloon.

8. A method according to claim 7, wherein said ablating is completed with a laser.

9. A method according to claim 8, wherein said forming said pores comprises punching said pores with a micropunch.

10. A method according to claim 1, further comprising mounting a stent on the balloon.

11. A balloon catheter assembly comprising:
    a catheter shaft; and
    a balloon mounted on the catheter shaft, the catheter shaft being configured to deliver an inflation fluid to the balloon, the balloon comprising
    a polymer selected from the group consisting of polyamide, polyether block amide, polyethylene, and polyethylene terephthalate, and
    a plurality of pores in the polymer, the pores being constructed and arranged to block fluid from passing therethrough when the balloon is inflated by the fluid.

12. A balloon catheter assembly according to claim 11, wherein the pores have an average diameter of less than about 500 microns.

13. A balloon catheter assembly according to claim 12, wherein the pores have an average diameter of greater than about 0.1 micron and less than about 400 microns.

14. A balloon catheter assembly according to claim 13, wherein the pores have an average diameter of between about 1 micron and about 100 microns.

15. A balloon catheter assembly according to claim 11, wherein the balloon has a pore density of about 100 pores per cm2 to about 1,000,000 pores per cm2.

16. A balloon catheter assembly according to claim 11, further comprising a stent mounted on the balloon.

* * * * *